United States Patent
Sakai et al.

(10) Patent No.: US 7,655,122 B2
(45) Date of Patent: Feb. 2, 2010

(54) OXYGEN CONCENTRATION DETECTING ELEMENT

(75) Inventors: Shoichi Sakai, Gunma (JP); Futoshi Ichiyanagi, Gunma (JP); Junji Onozuka, Gunma (JP); Goji Matsumoto, Gunma (JP)

(73) Assignee: Hitachi, Ltd., Tokyo (JP)

( * ) Notice: Subject to any disclaimer, the term of this patent is extended or adjusted under 35 U.S.C. 154(b) by 757 days.

(21) Appl. No.: 11/016,916

(22) Filed: Dec. 21, 2004

(65) Prior Publication Data
US 2005/0158459 A1 Jul. 21, 2005

(30) Foreign Application Priority Data
Jan. 19, 2004 (JP) ............... 2004-010132

(51) Int. Cl.
*G01N 27/26* (2006.01)
(52) U.S. Cl. .............. 204/424; 204/421; 204/431
(58) Field of Classification Search ........... 204/424, 204/421, 426, 274
See application file for complete search history.

(56) References Cited

U.S. PATENT DOCUMENTS

| | | | |
|---|---|---|---|
| 4,814,061 A * | 3/1989 | Blumenthal et al. ......... 204/410 |
| 4,980,042 A | 12/1990 | Shiomi et al. |
| 6,241,865 B1 * | 6/2001 | Cappa et al. ............... 204/427 |
| 6,426,631 B1 * | 7/2002 | Akiyama et al. ............ 324/464 |
| 2003/0213692 A1 | 11/2003 | Sakai et al. |
| 2005/0274613 A1 * | 12/2005 | Sakai et al. ............... 204/408 |

FOREIGN PATENT DOCUMENTS

| | | |
|---|---|---|
| DE | 44 24 529 A1 | 1/1995 |
| EP | 1 026 502 A | 8/2000 |
| EP | 1 348 950 A2 | 10/2003 |
| JP | S61-272649 * | 12/1896 |
| JP | 61 172054 A | 8/1986 |
| JP | 7-27737 A | 1/1995 |

* cited by examiner

*Primary Examiner*—Nam X Nguyen
*Assistant Examiner*—J. Christopher Ball
(74) *Attorney, Agent, or Firm*—Antonelli, Terry, Stout & Kraus, LLP.

(57) ABSTRACT

An oxygen concentration detecting element including a base member made of an electrically insulating material, a heater disposed on an outer surface of the base member, the heater being adapted to generate heat upon being energized, and an oxygen detecting unit disposed in an offset position on the outer surface of the base member in which the oxygen detecting unit is prevented from overlapping with the heater, the oxygen detecting unit including a solid electrolyte layer and a pair of electrodes between which the solid electrolyte layer is disposed.

25 Claims, 5 Drawing Sheets

OXYGEN CONCENTRATION DETECTING ELEMENT

BACKGROUND OF THE INVENTION

The present invention relates to an oxygen concentration detecting element useable for an oxygen sensor for sensing oxygen concentration in exhaust gas.

Generally, automobiles are equipped with an oxygen sensor in an exhaust pipe coupled to an engine. The oxygen sensor is adapted for sensing oxygen concentration in exhaust gas emitted from the engine. An air/fuel ratio is feedback controlled to a stoichiometric ratio, i.e., 14.7, on the basis of the oxygen concentration sensed by the oxygen sensor.

FIG. 5 shows a longitudinal cross-section of an oxygen concentration detecting element of a related art. As illustrated in FIG. 5, oxygen concentration detecting element 100 includes base member 101, solid electrolyte layer 102 disposed outside base member 101, and porous layer 103 disposed on an outer surface of base member 101. Reference electrode 104 is disposed on an inner surface of solid electrolyte layer 102. Detecting electrode 105 is disposed on an outer surface of solid electrolyte layer 102. Solid electrolyte layer 102, reference electrode 104 and detecting electrode 105 cooperate to form oxygen detecting unit 120. Dense layer 106 with oxygen introduction window 106A covers outer surfaces of solid electrolyte layer 102 and detecting electrode 105 except a part of the outer surface of detecting electrode 105 which is exposed through oxygen introduction window 106A. Protecting layer 107 is disposed on an outer surface of dense layer 106 and the exposed part of the outer surface of detecting electrode 105. A flow of gas to be measured, for instance, an exhaust gas flowing from an engine into an exhaust pipe is introduced to the outside of dense layer 106 and protecting layer 107.

Base member 101 is constituted of cylindrical solid core rod 110, heater pattern 111 formed on an outer circumferential surface of core rod 110, and heater insulating layer 112 disposed on the outer circumferential surface of core rod 110 so as to cover heater pattern 111. Heater insulating layer 112 is made of an electrically insulating material and formed by printing. Thus, oxygen detecting unit 120 is overlaid on an outer surface of heater pattern 111.

Reference electrode 104 and detecting electrode 105 are made of a material having electrical conductivity and oxygen permeability. Reference electrode 104 and detecting electrode 105 have integrally formed leads, respectively. Only the lead of detecting electrode 105 is indicated at 113 in FIG. 5. An output voltage generated between reference electrode 104 and detecting electrode 105 is taken out through leads 113 and measured. Dense layer 106 is made of a material preventing oxygen in the gas to be measured from permeating therethrough. Protecting layer 107 is made of a material permitting oxygen in the gas to be measured to permeate therethrough but preventing harmful gases in the gas to be measured from permeating therethrough.

Operation of oxygen concentration detecting element 100 is explained below. When heater pattern 111 is energized to generate heat, the heat generated is transmitted to oxygen detecting unit 120 through heater insulating layer 112. Solid electrolyte layer 102 of oxygen detecting unit 120 is activated by the heat transmitted. Oxygen in the gas to be measured permeates through protecting layer 107 and detecting electrode 105 and reaches the outer surface of solid electrolyte layer 102. Oxygen in the atmosphere, acting as a reference, permeates through porous layer 103 and reference electrode 104 and reaches the inner surface of solid electrolyte layer 102. When there is a difference in oxygen concentration between the inner and outer surfaces of solid electrolyte layer 102, oxygen ions are transmitted through solid electrolyte layer 102 to produce electromotive force between reference electrode 104 and detecting electrode 105 depending upon the difference in oxygen concentration. As a result, an output voltage varying corresponding to the difference in oxygen concentration is obtained.

Japanese Patent Application First Publication No. 7-27737 describes such an oxygen concentration detecting element as explained in the related art.

SUMMARY OF THE INVENTION

However, oxygen concentration detecting element 100 of the related art has a laminated structure in which heater pattern 111 and oxygen detecting unit 120 which are made of materials having different coefficients of thermal expansion overlap one another via heater insulating layer 112. The difference in coefficient of thermal expansion will cause thermal stress between heater pattern 111 and oxygen detecting unit 120, whereby separation therebetween and cracks due to the separation will occur.

Further, in a case where respective leads 113 of reference electrode 104 and detecting electrode 105 are extended onto a portion of the outer surface of core rod 110 which is not covered with heater insulating layer 112, leads 113 must extend along a step formed between the portion of the outer surface of core rod 110 and a radially extending end surface of heater insulating layer 112. Since a thickness of heater insulating layer 112 is required to considerably increase in order to ensure insulation between heater pattern 111 and oxygen detecting unit 120, the step becomes larger so that a length of leads 113 is elongated. This will cause break in leads 113, reducing yield. Furthermore, printing must be repeated a great number of times in order to increase the thickness of heater insulating layer 112. This will cause increase in cost.

It is an object of the present invention to provide an oxygen concentration detecting element which can prevent occurrence of cracks in a heater pattern and an oxygen detecting unit due to thermal stress, improve yield of leads for a pair of electrodes, and reduce the number of times of printing of a heater insulating layer to thereby serve for cost saving.

The other objects and features of this invention will become understood from the following description with reference to the accompanying drawings.

In one aspect of the present invention, there is provided an oxygen concentration detecting element, comprising:

a base member made of an electrically insulating material;

a heater disposed on an outer surface of the base member, the heater being adapted to generate heat upon being energized; and an oxygen detecting unit disposed in an offset position on the outer surface of the base member in which the oxygen detecting unit is prevented from overlapping with the heater, the oxygen detecting unit including a solid electrolyte layer and a pair of electrodes between which the solid electrolyte layer is disposed.

In a further aspect of the present invention, there is provided a method of producing an oxygen concentration detecting element, the oxygen concentration detecting element including a base member, a heater disposed on an outer surface of the base member, and an oxygen detecting unit disposed in an offset position on the outer surface of the base member in which the oxygen detecting unit is prevented from overlapping with the heater, the oxygen detecting unit including a solid electrolyte layer and a pair of electrodes between which the solid electrolyte layer is disposed, the method comprising:

forming the base member by molding an electrically insulating material;

forming the heater by screen-printing a paste made of an exothermic material on a first predetermined region of an outer surface of the base member, while rotating the base member;

forming one electrode with leads by screen-printing a conductive paste on a second predetermined region of the outer surface of the base member which is offset from the first predetermined region, while rotating the base member;

forming a solid electrolyte layer by screen-printing a paste material on the outer surfaces of the one electrode, while rotating the base member; and forming the other electrode with leads by screen-printing a conductive paste on an outer surface of the solid electrolyte layer, while rotating the base member.

DETAILED DESCRIPTION OF THE INVENTION

Figure 1:
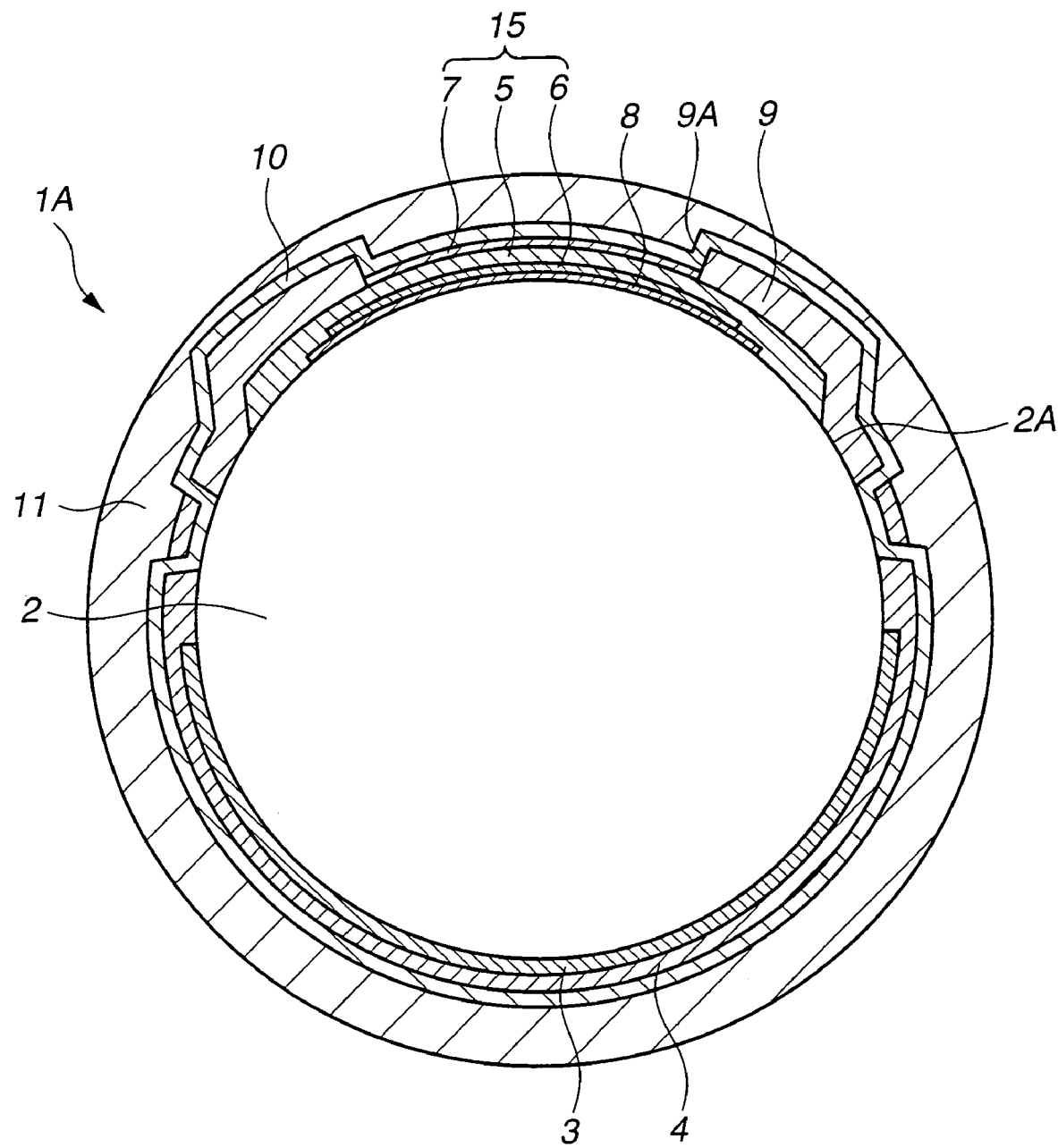
FIG. 1 is a cross-sectional view of a first embodiment of an oxygen concentration detecting element according to the present invention, taken in a direction perpendicular to an axial direction of the oxygen concentration detecting element.
Figure 2:
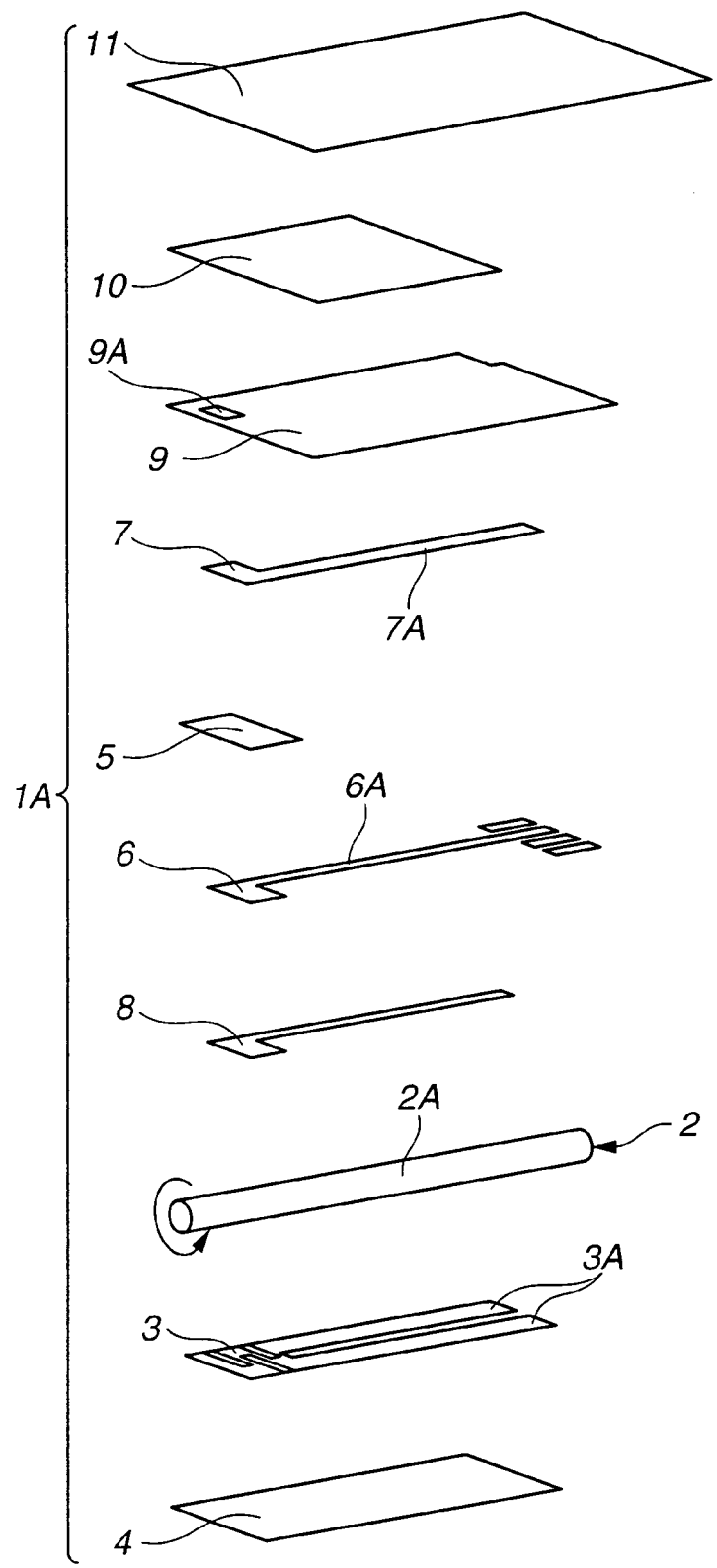
FIG. 2 is an exploded view of the first embodiment, for explanation of a method of producing the first embodiment.
Figure 3:
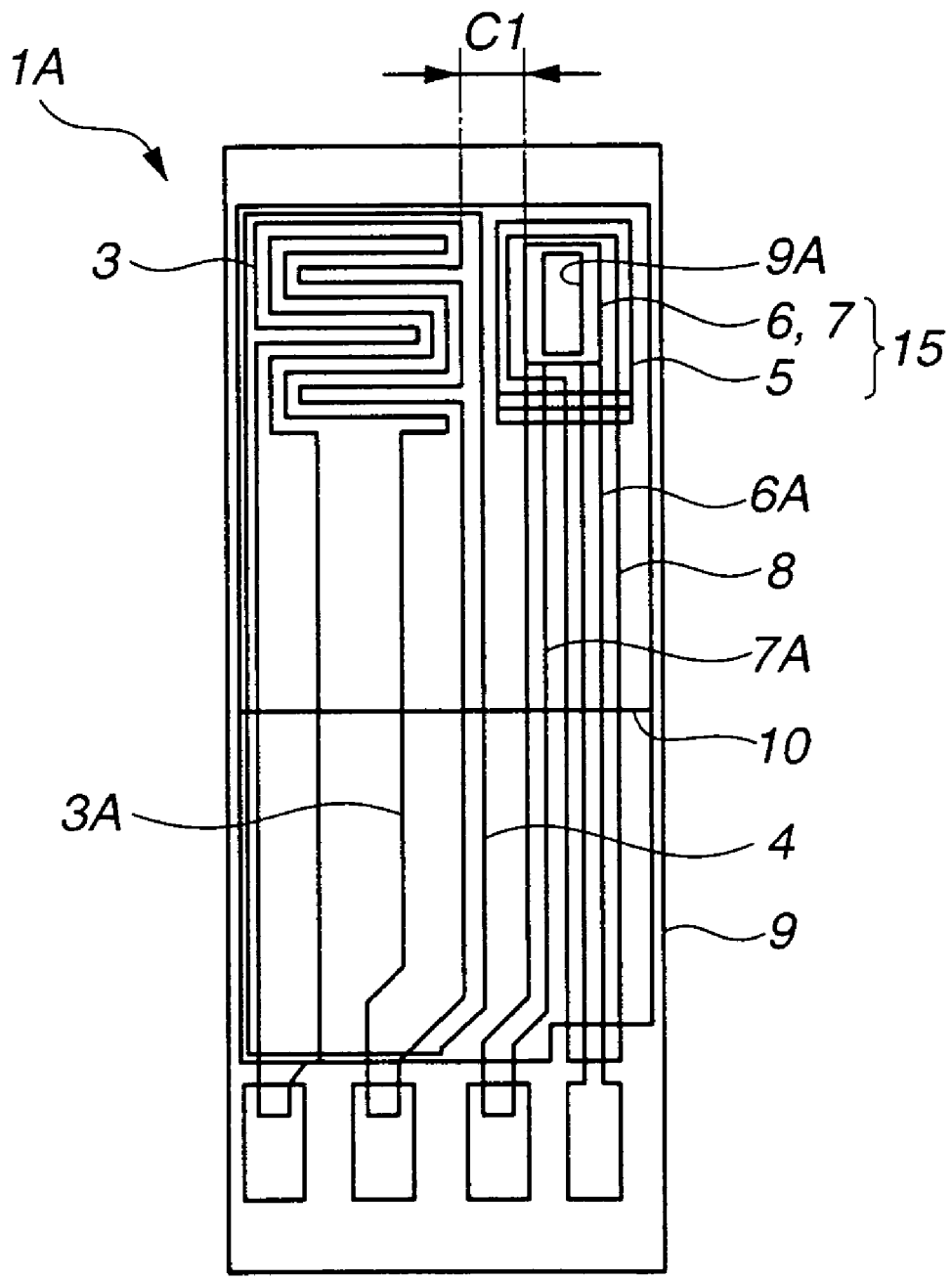
FIG. 3 is an extend elevation of the first embodiment.

Referring to FIGS. 1 to 3, a first embodiment of an oxygen concentration detecting element according to the present invention now is explained. As illustrated in FIG. 1, oxygen concentration detecting element 1A includes base member 2, heater 3 disposed on outer surface 2A of base member 2, and heater insulating layer 4 covering an entire outer surface of heater 3. Solid electrolyte layer 5 is disposed in a circumferentially offset position relative to heater 3 on outer surface 2A of base member 2 via reference electrode 6 and stress damping layer 8. Reference electrode 6 is disposed on an inner surface of solid electrolyte layer 5. Detecting electrode 7 is disposed on an outer surface of solid electrolyte layer 5. Stress damping layer 8 is disposed between outer surface 2A of base member 2 and an inner surface of reference electrode 6. Dense layer 9 with window 9A is disposed on the outer surfaces of solid electrolyte layer 5 and detecting electrode 7. Print protecting layer 10 is disposed on outer surfaces of dense layer 9, detecting electrode 7 and heater insulating layer 4. Spinel protecting layer 11 is disposed on an entire outer surface of print protecting layer 10.

Specifically, base member 2 is made of an electrically insulating material, for instance, a ceramic material such as alumina. Base member 2 is a solid core rod having a cylindrical rod shape having circumferential outer surface 2A. Heater 3 is in the form of a heater pattern and made of an exothermic and conductive material, such as tungsten and platinum, which generates heat upon being energized. Heater 3 has integrally formed leads 3A as shown in FIG. 2. When energized through leads 3A, heater 3 produces heat to cause temperature rise of solid electrolyte layer 5 and thereby activate solid electrolyte layer 5. Heater insulating layer 4 is made of an electrically insulating material such as, for instance, alumina, and electrically insulates heater 3 from the surroundings.

Solid electrolyte layer 5 has an oxygen-ion conductivity and is made of a paste material. The paste material may be prepared from a mixture of yttria and zirconia blended together at a predetermined weight ratio. When activated, solid electrolyte layer 5 generates an electromotive force between reference electrode 6 and detecting electrode 7 which varies depending on a difference in oxygen concentration between sides of reference electrode 6 and detecting electrode 7. This causes oxygen ions to move in solid electrolyte layer 5 in a direction of a thickness of solid electrolyte layer 5. Namely, solid electrolyte layer 5, reference electrode 6 and detecting electrode 7 cooperate to form oxygen detecting unit 15 for converting the difference in oxygen concentration to the corresponding electric signal.

Oxygen detecting unit 15 is placed in an offset position on circumferential outer surface 2A of base member 2 in which oxygen detecting unit 15 is prevented from overlapping with heater 3 so as to prevent oxygen detecting unit 15 from suffering from thermal stress upon energizing heater 3. In this embodiment, oxygen detecting unit 15 is disposed in the offset position relative to heater 3 on circumferential outer surface 2A of base member 2 in a radial direction of base member 2. Specifically, oxygen detecting unit 15 is arranged radially diametrically opposed to heater 3 on circumferential outer surface 2A of base member 2. Oxygen detecting unit 15 is disposed offset from heater 3 with a clearance in the circumferential direction of base member 2 on circumferential outer surface 2A of base member 2. In this position, heater 3 and oxygen detecting unit 15 are prevented from suffering from thermal stress which will be caused due to difference in coefficient of thermal expansion thereof when heater 3 is energized to generate heat.

Each of reference electrode 6 and detecting electrode 7 is made of a material having electrical conductivity and oxygen gas permeability. Reference electrode 6 and detecting electrode 7 have leads 6A and 7A formed integrally therewith, respectively, as shown in FIG. 2. An output voltage produced between reference electrode 6 and detecting electrode 7 is led to a measurement section, not shown, via leads 6A and 7A. There is a clearance between heater 3 and reference electrode 6 and detecting electrode 7 in a circumferential direction of base member 2. The clearance is indicated as C1 in FIG. 3. The clearance may be 0.5 mm or more. FIG. 3 shows an extend elevation of oxygen concentration detecting element 1A, showing profiles of respective layers of oxygen concentration detecting element 1A.

Stress damping layer 8 is made of a mixture of zirconia and aluminum. Stress damping layer 8 acts for reducing a difference in thermal stress between solid electrolyte layer 5 and base member 2 which will occur during sintering of solid electrolyte layer 5. Further, stress damping layer 8 forms a gas relief passage for relieving the oxygen gas via a path (not shown) which is transmitted to reference electrode 6 through solid electrolyte layer 5.

Dense layer 9 is made of such a material as a ceramic material, e.g., alumina, which prevents oxygen in the gas to be measured from permeating therethrough. Dense layer 9 with window 9A covers the entire outer surface of solid electrolyte layer 5 except a portion of the outer surface of solid electrolyte layer 5 which is exposed through window 9A to the gas to be measured, via detecting electrode 7, print protecting layer 10 and spinel protecting layer 11. Oxygen in the gas to be measured is permitted to enter detecting electrode 7 through only window 9A of dense layer 9.

Print protecting layer 10 covers the outer surface of detecting electrode 7 which is exposed to the outside through window 9A of dense layer 9. Print protecting layer 10 is made of a porous material that prevents harmful gases and dusts in the gas to be measured from permeating therethrough, but allows oxygen in the gas to be measured to permeate therethrough. The porous material may be formed from a mixture of alumina and magnesium oxide.

Spinel protecting layer 11 is made of a porous material that allows oxygen in the gas to be measured to permeate therethrough and has a porosity greater than that of print protecting layer 10.

Referring to FIG. 2, a method of producing oxygen concentration detecting element 1A of the first embodiment will be explained hereinafter. First, base member 2 is prepared by injection-molding a ceramic material, e.g., alumina, into the cylindrical core rod shape. Next, heater 3 is provided in the form of a heater pattern on a substantially half region of circumferential outer surface 2A of base member 2. Specifically, while rotating base member 2, a paste made of an exothermic material, e.g., platinum or tungsten, which generates heat upon being energized, is screen-printed on the substantially half region of circumferential outer surface 2A of base member 2. Subsequently, heater insulating layer 4 is formed by screen-printing on the substantially half region of circumferential outer surface 2A of base member 2 so as to cover an entire outer surface of heater 3. While rotating base member 2, a paste made of an electrically insulating material, e.g., alumina, is screen-printed on the substantially half region of circumferential outer surface 2A of base member 2 so as to cover the entire outer surface of heater 3.

Next, stress damping layer 8 is formed by screen-printing on an opposite half region of circumferential outer surface 2A of base member 2 which is diametrically opposed to the substantially half region of circumferential outer surface 2A in which heater 3 and heater insulating layer 4 are formed. While rotating base member 2, a paste material including zirconia and aluminum is screen-printed on the opposite half region of circumferential outer surface 2A of base member 2.

Then, reference electrode 6 with leads 6A is formed by screen-printing a conductive paste, e.g., a platinum paste, on an outer surface of stress damping layer 8, while rotating base member 2. Subsequently, solid electrolyte layer 5 is formed by screen-printing a paste material including zirconia and yttria on the outer surfaces of reference electrode 6 and stress damping layer 8, while rotating base member 2. Detecting electrode 7 with leads 7A is formed by screen-printing a conductive paste, e.g., a platinum paste, on the outer surface of solid electrolyte layer 5, while rotating base member 2.

Next, dense layer 9 with rectangular window 9A is formed by screen-printing on the outer surfaces of detecting electrode 7 and solid electrolyte layer 5. While rotating base member 2, a paste made of a ceramic material, e.g., alumina, is screen-printed on the outer surfaces of detecting electrode 7 and solid electrolyte layer 5 so as to cover the outer surfaces of detecting electrode 7 and solid electrolyte layer 5 except a central portion of the outer surface of detecting electrode 7. The paste is thus screen-printed so as to form dense layer 9 with window 9A through which the central portion of the outer surface of detecting electrode 7 is exposed. The exposed central portion of detecting electrode 7 acts as an effective portion of the electrode.

Subsequently, print protecting layer 10 is formed by screen-printing on the outer surfaces of dense layer 9 and heater insulating layer 4 so as to cover an entire circumferential region of circumferential outer surface 2A of base member 2. While rotating base member 2, a paste material having oxygen permeability and harmful gas impermeability, e.g., a paste material of a mixture of alumina and magnesium oxide, is screen-printed on the outer surfaces of dense layer 9 and heater insulating layer 4 so as to extend over the entire circumferential region of circumferential outer surface 2A of base member 2. Next, spinel protecting layer 11 is formed by screen-printing on an outer surface of print protecting layer 10. While rotating base member 2, a paste material for spinel protecting layer 11 is screen-printed on an outer surface of print protecting layer 10 so as to extend over the entire circumferential region of circumferential outer surface 2A of base member 2. The sequential operation of screen-printing is thus completed. As a result, a green body of oxygen concentration detecting element 1A which has the multilayered structure is prepared.

Next, the green body is baked at high temperature and sintered into an integral body. Oxygen concentration detecting element 1A is thus produced and then installed in an oxygen sensor, not shown.

An operation of oxygen concentration detecting element 1A will be explained hereinafter in a case where an oxygen sensor using oxygen concentration detecting element 1A is disposed in an exhaust pipe coupled to an engine. The oxygen sensor is arranged such that exhaust gas passing through the exhaust pipe is allowed to flow along a circumferential outer surface of oxygen concentration detecting element 1A, and atmosphere as a reference is introduced to the inside of oxygen concentration detecting element 1A to reach reference electrode 6 through stress damping layer 8. Heater 3 is energized to generate heat required for increasing a temperature of the whole oxygen concentration detecting element 1A to a predetermined temperature at which solid electrolyte layer 5 is activated.

In this condition, the exhaust gas emitted from the engine flows into the exhaust pipe and passes by the circumferential outer surface of oxygen concentration detecting element 1A. Oxygen in the exhaust gas is introduced into solid electrolyte layer 5 activated, via spinel protecting layer 11, print protecting layer 10 and detecting electrode 7. On the other hand, oxygen in the atmosphere is introduced and collected around reference electrode 6. When there occurs a difference in oxygen concentration between inner and outer surfaces of solid electrolyte layer 5, oxygen ions are moved in solid electrolyte layer 5 to thereby produce an electromotive force between reference electrode 6 and detecting electrode 7. As a result, an output voltage that varies depending upon the oxygen concentration difference is obtained.

Oxygen concentration detecting element 1A of the first embodiment has the following effects. With the above-explained offset, namely, non-overlapping, arrangement of heater 3 and oxygen detecting unit 15 on circumferential outer surface 2A of base member 2, heater 3 and oxygen detecting unit 15 can be prevented from suffering from thermal stress which will be caused when heater 3 is energized to generate heat. This prevents occurrence of cracks in heater 3 or oxygen detecting unit 15. Specifically, in contrast to the oxygen concentration detecting element of the related art, heater 3 and oxygen detecting unit 15 are placed in the offset position, whereby heater 3 and oxygen detecting unit 15 are not adhered to each other via a mutually contacting surface therebetween. This suppresses thermal stress that will be caused on the adhered surfaces due to difference in coefficient of thermal expansion of heater 3 and oxygen detecting unit 15 when heater 3 is energized to generate heat. Accordingly, occurrence of cracks in heater 3 and oxygen detecting unit 15 which will be caused by the thermal stress can be prevented.

Further, as seen from FIG. 2, leads 6A of reference electrode 6 and leads 7A of detecting electrode 7 are respectively disposed indirectly and directly on circumferential outer surface 2A of base member 2 without extending on heater insulating layer 4. Therefore, leads 6A and 7A can be arranged without extending along a step between a radially extending end surface of heater insulating layer 4 and circumferential outer surface 2A of base member 2, in contrast to the related art. This avoids the necessity for increasing length of leads 6A and 7A to thereby improve yields of leads 6A and 7A and result in cost-saving.

Figure 5:
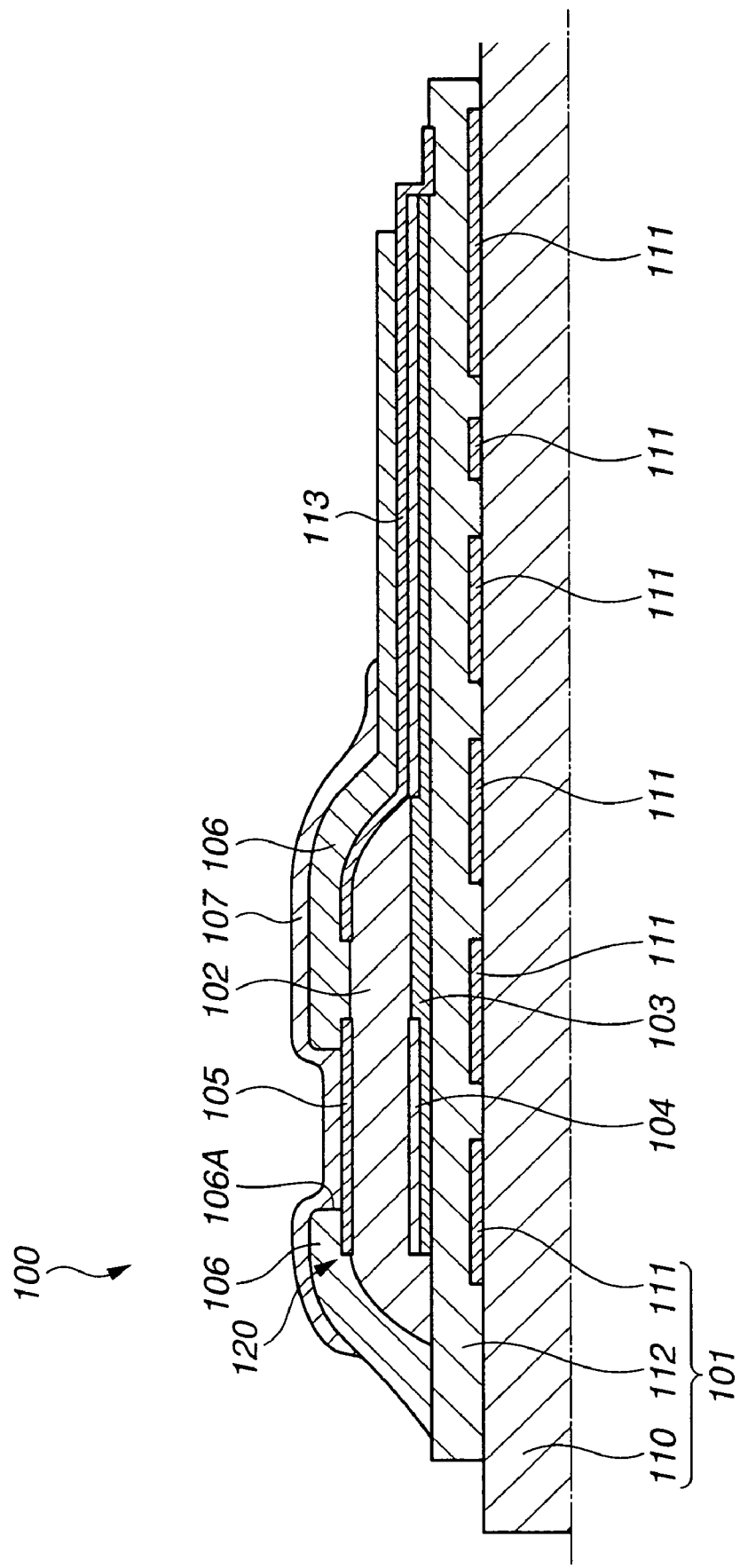
FIG. 5 is a longitudinal cross-section of a part of a conventional oxygen concentration detecting element.

Further, since heater 3 and oxygen detecting unit 15 are arranged in the circumferentially offset position, insulation therebetween can be achieved even when a thickness of heater insulating layer 4 is reduced. This serves for reducing the number of printing of heater insulating layer 4, and therefore, reducing the production cost of oxygen concentration detecting element 1A. In contrast, since the oxygen concentration detecting element of the related art as shown in FIG. 5 has the lamination arrangement of heater pattern 111 and oxygen detecting unit 120, heater insulating layer 112 having a larger thickness is formed between heater patter 111 and oxygen detecting unit 120 by conducting printing of heater insulating layer 112 a plurality of times. This leads to increase in cost. Thus, oxygen concentration detecting element 1A of the present invention includes the offset arrangement of heater 3 and oxygen detecting unit 15 and the arrangement of heater insulating layer 4 having a relatively small thickness and covering the outer surface of heater 3, whereby the insulation between heater 3 and oxygen detecting unit 15 can be ensured. As a result, oxygen concentration detecting element 1A of the present invention serves for reducing the number of printing of heater insulating layer 4 and the production cost.

Further, since base member 2 has the cylindrical rod shape having circumferential outer surface 2A, oxygen concentration can be detected with stable accuracy without being affected by influence of a direction of oxygen concentration detecting element 1A in a mounted state or influence of a direction of a flow of gas to be measured.

Further, heater 3 and oxygen detecting unit 15 are placed in the radially diametrically opposite positions on circumferential outer surface 2A of base member 2. Therefore, oxygen concentration detecting element 1A can have a compact structure with a sufficient clearance between heater 3 and oxygen detecting unit 15 to attain insulation therebetween. Furthermore, heater 3 and oxygen detecting unit 15 are formed by screen-printing in the circumferentially offset positions on the same surface, namely, on circumferential outer surface 2A of base member 2. Therefore, oxygen concentration detecting element 1A can be readily produced.

Further, heater 3 and reference electrode 6 and detecting electrode 7 of oxygen detecting unit 15 are disposed with circumferential clearance C1 of 0.5 mm or more therebetween. Thus, there are sufficient intervals for insulation between heater 3 and reference electrode 6 and detecting electrode 7. This can reduce a thickness of heater insulating layer 4 to thereby reduce the number of printing of insulating layer 4 and the production cost.

Furthermore, since stress damping layer 8 is interposed between base member 2 and oxygen detecting unit 15, a difference in thermal stress caused between base member 2 and solid electrolyte layer 5 of oxygen detecting unit 15 upon sintering solid electrolyte layer 5 can be reduced.

Figure 4:
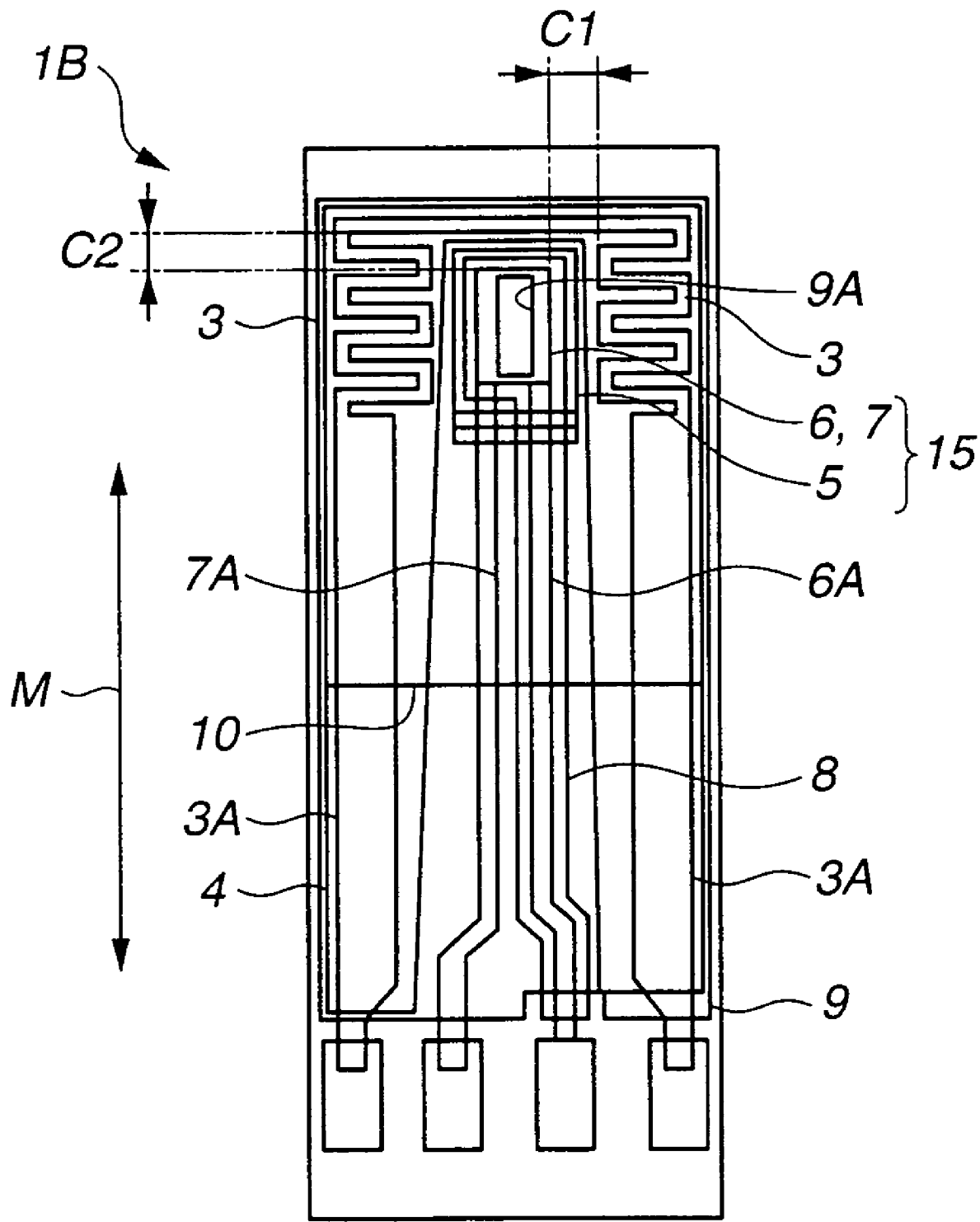
FIG. 4 is a view similar to FIG. 1, but showing a second embodiment of the oxygen concentration detecting element according to the present invention.

Referring to FIG. 4, a second embodiment of the oxygen concentration detecting element of the present invention is explained. FIG. 4 shows an extend elevation of oxygen concentration detecting element 1B of the second embodiment, showing profiles of respective layers of oxygen concentration detecting element 1B. The second embodiment differs in arrangement of heater 3 and oxygen detecting unit 15 from the first embodiment. Like reference numerals denote like parts, and therefore, detailed explanations thereof are omitted.

As illustrated in FIG. 4, heater 3 and oxygen detecting unit 15 of oxygen concentration detecting element 1B are disposed offset from each other in axial direction M of base member 2 and in the circumferential direction thereof on circumferential outer surface 2A. Further, there are circumferential clearance C1 and axial clearance C2 between heater 3 and reference electrode 6 and detecting electrode 7 of oxygen detecting unit 15. Each of clearances C1 and C2 may be 0.5 mm or more. Similar to oxygen concentration detecting element 1A of the first embodiment, heater 3 and oxygen detecting unit 15 of oxygen concentration detecting element 1B are placed in the offset position where heater 3 and oxygen detecting unit 15 are prevented from radially overlapping each other.

Oxygen concentration detecting element 1B of the second embodiment is produced by a method similar to the method explained in the first embodiment except forming heater 3, reference electrode 6 and detecting electrode 7 in the respective axially and circumferentially offset positions on circumferential outer surface 2A of base member 2.

With the offset arrangement of heater 3 and oxygen detecting unit 15 of oxygen concentration detecting element 1B, the second embodiment can have a compact structure with a sufficient clearance between heater 3 and oxygen detecting unit 15 to attain insulation therebetween. Further, heater 3 and oxygen detecting unit 15 of oxygen concentration detecting element 1B are formed by screen-printing in the relatively offset positions on the same surface, namely, on circumferential outer surface 2A of base member 2. Oxygen concentration detecting element 1B, therefore, can be readily produced.

Further, reference electrode 6 and detecting electrode 7 of oxygen detecting unit 15 of oxygen concentration detecting element 1B are disposed offset from heater 3 with clearances C1 and C2 as shown in FIG. 4, whereby similar to the first embodiment, there are sufficient intervals for insulation between heater 3 and electrodes 6 and 7. This can reduce a thickness of heater insulating layer 4 to thereby reduce the number of printing of insulating layer 4 and the production cost.

Furthermore, the present invention can be modified as explained below, in which the same functions and effects as those of the first and second embodiments can be obtained. The shape of window 9A of dense layer 9 is not limited to the rectangular shape of the first and second embodiments, and may be a circular shape, an elliptic shape, a triangular shape and a polygonal shape including a pentagon. Further, the shape of base member 2 is not limited to the cylindrical rod shape, and may be other shapes having a flat outer surface.

This application is based on a prior Japanese Patent Application No. 2004-010132 filed on Jan. 19, 2004. The entire contents of the Japanese Patent Application No. 2004-010132 is hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. An oxygen concentration detecting element, comprising:
    a base member made of an electrically insulating material;
    a heater disposed on at least one outer surface of the base member, the heater being adapted to generate heat upon being energized; and
    an oxygen detecting unit disposed in an offset position on the at least one outer surface of the base member in which the oxygen detecting unit is prevented from overlapping with the heater, the oxygen detecting unit including a solid electrolyte layer and a pair of electrodes between which the solid electrolyte layer is disposed,
    wherein the heater and the solid electrolyte layer are disposed on the at least one outer surface of the base member so as to be separate from each other and out of contact with each other.

2. The oxygen concentration detecting element as claimed in claim 1, wherein the base member has a cylindrical rod shape, the at least one outer surface of the base member being a circumferential outer surface.

3. The oxygen concentration detecting element as claimed in claim 2, wherein the oxygen detecting unit is prevented from overlapping with the heater in a radial direction of the base member.

4. The oxygen concentration detecting element as claimed in claim 2, wherein the oxygen detecting unit is offset from the heater in a circumferential direction of the base member.

5. The oxygen concentration detecting element as claimed in claim 3, wherein the oxygen detecting unit is diametrically opposed to the heater.

6. The oxygen concentration detecting element as claimed in claim 4, wherein the pair of electrodes of the oxygen detecting unit are offset from the heater with a circumferential clearance.

7. The oxygen concentration detecting element as claimed in claim 2, wherein the oxygen detecting unit is offset from the heater in an axial direction of the base member.

8. The oxygen concentration detecting element as claimed in claim 7, wherein the heater and the pair of electrodes of the oxygen detecting unit are arranged with an axial clearance therebetween.

9. The oxygen concentration detecting element as claimed in claim 1, further comprising a stress damping layer disposed between the base member and one of the pair of electrodes of the oxygen detecting unit, the stress damping layer being adapted for reducing a difference in thermal stress caused between the base member and the solid electrolyte layer when the solid electrolyte layer is sintered.

10. The oxygen concentration detecting element as claimed in claim 1, further comprising a heater insulating layer covering an outer surface of the heater.

11. The oxygen concentration detecting element as claimed in claim 10, wherein the pair of electrodes have leads integrally formed therewith, respectively, the leads being disposed on the at least one outer surface of the base member without extending on the heater insulating layer, respectively.

12. An oxygen concentration detecting element, comprising:
    a base member made of an electrically insulating material;
    a heater disposed on at least one outer surface of the base member and arranged to generate heat upon being energized; and
    an oxygen detecting unit including a solid electrolyte layer arranged between a pair of electrodes;
    wherein the oxygen detecting unit is disposed in a position on the at least one outer surface of the base member separated from the heater, such that the oxygen detecting unit does not contact the heater.

13. The oxygen concentration detecting element as claimed in claim 12, wherein the base member has a cylindrical rod shape, and the at least one outer surface of the base member is a circumferential outer surface.

14. The oxygen concentration detecting element as claimed in claim 13, wherein the oxygen detecting unit is prevented from overlapping with the heater in a radial direction of the base member.

15. The oxygen concentration detecting element as claimed in claim 13, wherein the oxygen detecting unit is offset from the heater in a circumferential direction of the base member.

16. The oxygen concentration detecting element as claimed in claim 14, wherein the oxygen detecting unit is diametrically opposed to the heater.

17. The oxygen concentration detecting element as claimed in claim 15, wherein the pair of electrodes of the oxygen detecting unit are offset from the heater with a circumferential clearance.

18. The oxygen concentration detecting element as claimed in claim 13, wherein the oxygen detecting unit is offset from the heater in an axial direction of the base member.

19. The oxygen concentration detecting element as claimed in claim 18, wherein the heater and the pair of electrodes of the oxygen detecting unit are arranged with an axial clearance therebetween.

20. The oxygen concentration detecting element as claimed in claim 12, comprising a stress damping layer disposed between the base member and one of the pair of electrodes of the oxygen detecting unit, and the stress damping layer is arranged so as to reduce a thermal stress between the base member and the solid electrolyte layer when the solid electrolyte layer is sintered.

21. The oxygen concentration detecting element as claimed in claim 12, comprising a heater insulating layer covering an outer surface of the heater.

22. The oxygen concentration detecting element as claimed in claim 21, wherein the pair of electrodes has a respective pair of leads integrally formed therewith, the pair of leads being disposed on the at least one outer surface of the base member without extending on the heater insulating layer.

23. The oxygen concentration detecting element as claimed in claim 1, wherein the heater is disposed on an outermost surface of the base member.

24. The oxygen concentration detecting element as claimed in claim 2, wherein the heater is disposed on the outer circumferential surface of the cylindrical rod shape base member.

25. The oxygen concentration detecting element as claimed in claim 12, wherein the heater is disposed on an outermost surface of the base member.

* * * * *